United States Patent
Hyun Yoo et al.

(10) Patent No.: US 12,345,699 B2
(45) Date of Patent: Jul. 1, 2025

(54) CONTACTLESS INSPECTION OF REPRODUCTIVE CELLULAR STRUCTURES USING OPTICAL MEASUREMENT OF BIOMECHANICAL PROPERTIES

(71) Applicant: Intelon Optics, Inc., Lexington, MA (US)

(72) Inventors: Jang Lawrence Hyun Yoo, Los Angeles, CA (US); Kwangsup Shin, Bedford, MA (US); Yen-Wei Lin, Natick, MA (US)

(73) Assignee: Intelon Optics, Inc., Lexington, MA (US)

( * ) Notice: Subject to any disclaimer, the term of this patent is extended or adjusted under 35 U.S.C. 154(b) by 1093 days.

(21) Appl. No.: 17/188,972

(22) Filed: Mar. 1, 2021

(65) Prior Publication Data

US 2021/0270810 A1    Sep. 2, 2021

Related U.S. Application Data

(60) Provisional application No. 62/982,368, filed on Feb. 27, 2020.

(51) Int. Cl.
*G01N 33/483* (2006.01)
*G01N 21/63* (2006.01)
(Continued)

(52) U.S. Cl.
CPC ....... *G01N 33/4833* (2013.01); *G01N 21/636* (2013.01); *G06F 17/18* (2013.01); *G01N 2021/638* (2013.01)

(58) Field of Classification Search
CPC .......... G01N 33/4833; G01N 33/5026; G01N 33/5029; G01N 33/5088; G01N 33/54373;
(Continued)

(56) References Cited

U.S. PATENT DOCUMENTS 9,829,482 B2 *  11/2017  An ..................... G01N 15/1434
10,031,123 B2 *  7/2018  Zarnescu ............. A61B 17/435
(Continued)

FOREIGN PATENT DOCUMENTS

KR   10-2016-0043089 A   4/2016
WO       2013-138513 A1   9/2013
WO       2019-089531 A1   5/2019

OTHER PUBLICATIONS

Raghunathan et al. Journal of Biomedical Optics, vol. 22(8), Aug. 2017, pp. 086013-1 to 086013-6.*
(Continued)

*Primary Examiner* — Maureen Wallenhorst
(74) *Attorney, Agent, or Firm* — United One Law Group LLC; Kongsik Kim; Jhongwoo Peck

(57) ABSTRACT

A method of measuring at least one biomechanical property of a reproductive cellular structure is provided. The method includes illuminating the reproductive cellular structure with radiation; detecting at least a portion of radiation scattered from the illuminated reproductive cellular structure; analyzing a frequency spectrum of the detected scattered radiation to identify at least one Brillouin frequency shift in the frequency spectrum; and determining the at least one biomechanical property based on the Brillouin frequency shift. The method further includes determining a viability index of the reproductive cellular structure based on the at least one biomechanical property.

16 Claims, 7 Drawing Sheets

(51) Int. Cl.
*G01N 33/50* (2006.01)
*G06F 17/18* (2006.01)

(58) Field of Classification Search
CPC .. G01N 21/636; G01N 21/1702; G01N 21/25; G01N 21/47; G01N 2021/638; A61B 2503/02; A61B 2503/42; A61B 5/0075; A61B 5/4362; A61B 5/4343
USPC ........ 436/63, 65, 164, 171, 906; 435/29, 31, 435/806
See application file for complete search history.

(56) References Cited

U.S. PATENT DOCUMENTS

| | | | |
|---|---|---|---|
| 2007/0162992 A1* | 7/2007 | Burns | G01R 33/465 435/325 |
| 2018/0120228 A1 | 5/2018 | Racowsky et al. | |
| 2018/0160898 A1 | 6/2018 | Yoo et al. | |
| 2018/0172572 A1* | 6/2018 | Prien | G01N 33/483 |
| 2020/0018685 A1 | 1/2020 | Scarcelli et al. | |

OTHER PUBLICATIONS

Prevedel et al. Nature Methods, vol. 16, Oct. 2019, pp. 969-977.*
Mattana et al. Light: Science & Applications, vol. 7, Oct. 12, 2017, pp. 1-9.*
Troyanova-Wood et al., "Brillouin microspectroscopy assessment of tissue differentiation during embryonic development," Society of Photo-Optical Instrumentation Engineers (SPIE), Proceedings vol. 10043, "Diagnosis and Treatment of Diseases in the Breast and Reproductive System," Feb. 20, 2017, 1004311.
Meng et al., "Watching embryonic development in a new light: elasticity specific imaging with dual Brillouin/Raman microspectroscopy," Society of Photo-Optical Instrumentation Engineers (SPIE), Proceedings vol. 9716, "Optical Methods in Developmental Biology IV," May 2, 2016, 97160L.
Zhang et al., "Non-invasive structural and biomechanical imaging of the developing embryos (Conference Presentation)," Society of Photo-Optical Instrumentation Engineers (SPIE), Proceedings vol. 10067, "Optical Elastography and Tissue Biomechanics IV," Apr. 24, 2017, 100670W.
Yanez et al., "Human oocyte developmental potential is predicted by mechanical properties within hours after fertilization," Nature Communications, Feb. 24, 2016, vol. 7, No. 10809.
International Search Report and Written Opinion, PCT/US2021/020312, dated Jun. 21, 2021, 12 pages.

* cited by examiner

CONTACTLESS INSPECTION OF REPRODUCTIVE CELLULAR STRUCTURES USING OPTICAL MEASUREMENT OF BIOMECHANICAL PROPERTIES

CROSS-REFERENCE TO RELATED APPLICATIONS

The present application claims priority to U.S. Provisional Application No. 62/982,368, filed on Feb. 27, 2020, which application is incorporated herein by reference in its entirety.

TECHNICAL FIELD

The present disclosure relates to reproductive cellular structure inspection, and more particularly, to contactless inspection of reproductive cellular structures using optical measurement of biomechanical properties.

RELATED ART

In vitro fertilization (IVF) is performed to aid individuals with sterility and infertility. Seeking help from fertility clinics is advised for a woman who has had more than one miscarriage; a woman under 35 years of age who has not conceived after 12 months of copulation without contraceptives; a woman over 35 years of age who has not conceived after 6 months of copulation without contraceptives; or a man who has a poor semen analysis. Some of the common services and treatments provided by a fertility clinic include preliminary tests, prescribing fertility medications and hormones, surgeries and assisted reproductive technology methods, which can include intrauterine insemination (IUI) and IVF.

The strong demand for IVF technologies today is likely due to several reasons, including an increase in the number of single mothers as well as the average age of new potential mothers; growing obesity that can cause hormonal imbalances and reproductive problems in women (about 35% of adults in the U.S. suffer from obesity, which can lead to conceiving problems); lower sperm quality in men (a decrease of sperm quality has been observed and documented in the U.S. and Europe for decades (Fetteers, 2018), and recently in developing countries (Huang et al., 2017; Sengupta et al., 2017); decreasing fertility of women (a decrease of fertility rate globally, especially in the most highly industrialized countries, is well-documented (Skakkebaek et al., 2019). According to statistics in the U.S., the live birth success rate for women under 35 is around 40%, but it drops sharply for women over 42 years old to only 4%.); and an increased demand for the LGBT groups seeking fertility assistance.

The market value for fertility clinics in the U.S. was $3.0 billion in 2012 and is expected to reach $4.5 billion by 2022. From 2017 to 2022, the annual growth rate is expected to be 4.6% (BCC, 2018). As of 2016, most fertility clinics in the U.S. provide all three major services including diagnostics, surgeries and Assisted Reproductive Technologies (ARTs). ART takes about 70% by share of the services provided by fertility clinics with an estimated market value of $2.4 billion. Diagnostic services and surgeries have estimated values of $0.9 billion and $0.2 billion, respectively (BCC, 2018). ARTs are further divided into in-vitro fertilization (IVF), gamete intrafallopian transfer (GIFT), donor ova, donor sperms, surrogate carrier, and the like. Among these, IVF takes an overwhelming 89.9% of the share, or worth $2.2 billion value. In 2016, 230,000 IVF procedures were performed in the U.S. alone, and the number is increasing. This accounts for nearly half of all market share in the ART.

SUMMARY

The present disclosure generally provides methods and systems for contactless inspection or monitoring of reproductive cellular structures based on optical measurement of one or more of their biomechanical properties.

According to an exemplary embodiment of the present disclosure, a method may include measuring a biomechanical property of a reproductive cellular structure using an optical imaging technique, and assessing the potential of the reproductive cellular structure for achieving a successful pregnancy based on the measured biomechanical property.

The method may include one or more of the following features individually or in any combinations thereof. The optical imaging technique may measure the biomechanical property based on Brillouin spectroscopy. The biomechanical property may include a modulus of elasticity or a modulus of viscosity. The reproductive cellular structure may include one selected from the group consisting of an embryo, a morula, a blastula, gastrula, a zygote, an ovum, and an oocyte.

By way of example, the method may be performed to select an oocyte to be fertilized with a male gamete and/or to select a zygote to proceed further into in-vitro fertilization. The method may be performed to select an embryo to be transferred to a uterus. In some embodiments, the biomechanical property of the reproductive cellular structure may be measured at a sub-cellular resolution. Further, the biomechanical property may be scanned so as to map a spatial distribution thereof across the reproductive cellular structure.

According to an exemplary embodiment of the present disclosure, a method of measuring at least one biomechanical property of a reproductive cellular structure may include illuminating the reproductive cellular structure with radiation, detecting at least a portion of radiation scattered from the illuminated reproductive cellular structure, analyzing a frequency spectrum of the detected scattered radiation to identify at least one Brillouin frequency shift in the frequency spectrum, and determining the at least one biomechanical property based on the Brillouin frequency shift. Further, a viability index of the reproductive cellular structure may be determined based on the at least one biomechanical property.

One or more of the following features may be included individually or in any combinations thereof. The at least one biomechanical property may include a modulus of elasticity, a modulus of viscosity, or both, of at least a portion of the reproductive cellular structure. The modulus of elasticity M' may be determined using the following formula:

$$M' = \rho \left(\frac{\lambda}{2n}\right)^2 \Delta v_B^2$$

wherein $\Delta v_B$ is the Brillouin frequency shift, p is a density of the at least a portion of the reproductive cellular structure, λ is a vacuum wavelength of the radiation, and n is a refractive index of the at least a portion of the reproductive cellular structure. Further, a width of at least one Brillouin peak in the frequency spectrum of the detected scattered radiation may be measured to determine the modulus of viscosity M" using the following formula:

$$M'' = \rho\left(\frac{\lambda}{2n}\right)^2 \Delta v_B \Gamma_B$$

wherein $\Gamma_B$ is the width of the at least one Brillouin peak. Subsequently, a complex modulus M* may be determined using the following formula:

$M^* = M' + i\,M''$ wherein $i$ denotes a unit imaginary number which satisfies $i^2 = -1$.

For obtaining the frequency spectrum of the scattered radiation, a spectrometer may be utilized. Further, the illuminating radiation may be laser radiation, and the laser radiation may include at least one frequency component corresponding to a vacuum wavelength in a range of about 400 nm to about 800 nm. In some embodiments, radiation that is elastically scattered from the reproductive cellular structure may be filtered out to facilitate detection of the Brillouin frequency shift.

In some embodiments, the at least one biomechanical property of the reproductive cellular structure may be determined with a sub-cellular resolution, and therefore, the at least one biomechanical property may be determined at a plurality of sub-cellular locations of the reproductive cellular structure.

According to an exemplary embodiment of the present disclosure, a system for determining at least one biomechanical property of a reproductive cellular structure may include a radiation source for generating illuminating radiation, at least one optic for directing the illuminating radiation onto at least a portion of the reproductive cellular structure, a detector for detecting at least a portion of radiation scattered from the reproductive cellular structure, a spectrometer for generating a frequency spectrum of the detected scattered radiation, and an analyzer for processing the frequency spectrum to identify at least one Brillouin frequency shift. The Brillouin frequency shift may be utilized to determine the at least one biomechanical property.

One or more of the following features may be included individually or in any combinations thereof. The system may further include at least one radiation collecting optic for directing the at least a portion of the scattered radiation to the detector through an optical fiber. The system may also include a pinhole disposed upstream of the at least one radiation collecting optic to block out-of-focus lights. In some embodiments, a single-mode optical fiber may be employed to function as the pinhole, though in other embodiments multi-mode optical fibers may be used to transmit the scattered radiation to the detector.

In some embodiments, the system may be configured to optically characterize the biomechanical property of the reproductive cellular structure at a sub-cellular resolution. For such embodiments, the system may include an actuator to scan a light beam over at least a portion of the reproductive cellular structure to measure a Brillouin frequency shift at different locations of the reproductive cellular structure and correlate the measured Brillouin frequency shifts to a spatial distribution of the biomechanical property across the reproductive cellular structure.

Notably, the present disclosure is not limited to the combination of the elements as listed above and may be assembled in any combination of the elements as described herein. Other aspects of the disclosure are disclosed herein.

BRIEF DESCRIPTION OF THE DRAWINGS

A brief description of each drawing is provided to more sufficiently understand drawings used in the detailed description of the present disclosure.

Figure 1:
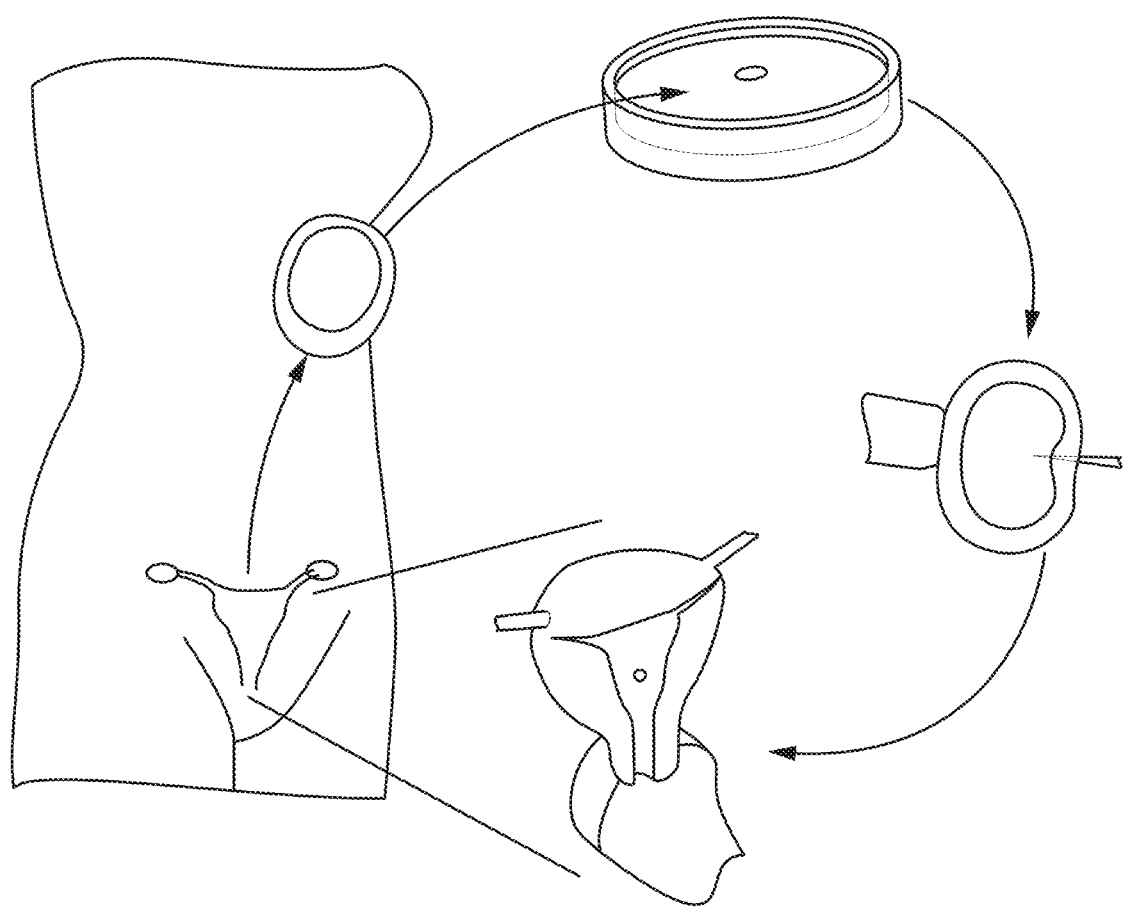
FIG. 1 shows a schematic of an IVF procedure with single sperm injection Intracytoplasmic Sperm Injection (ICSI)

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION

Various features of the present disclosure will become apparent with reference to the accompanying drawings and examples of embodiments described below in detail. However, the present disclosure is not limited to the disclosed embodiments and may be embodied in variations and modifications. The illustrative embodiments are provided merely to allow one of ordinary skill in the art to understand various features of the present disclosure, which will be defined by the scope of the claims. Accordingly, in some embodiments, well-known operations of a process, well-known structures, and well-known technologies will not be described in detail to avoid obscure understanding of the present disclosure. Throughout the specification, same reference numerals refer to same elements.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The term "reproductive cellular structure," as used herein refers to any sex cell, before or after fusing, such as an oocyte, ovum, and zygote, as well as more complex fused cellular structures such as an embryo, a morula, a blastula, gastrula, which are formed at different stages of reproduction.

The term "resolution," as used herein, refers a minimum spatial interval (e.g., distance) at which discrete measurements can be obtained on the cellular structures. The term "resolution," where the context indicates, may also refer to a minimum measurement accuracy (e.g., a minimum detectable frequency shift in terms of MHz).

The terms "light" and "radiation" are used herein interchangeably to refer to not only visible radiation but also radiation having a frequency in other portions of the electromagnetic spectrum, e.g., the infrared portion of the electromagnetic spectrum.

Aspects of the present disclosure may include determining one or more biomechanical properties of a reproductive cellular structure using an optical interrogating radiation, utilizing the biomechanical properties to improve the selection or screening procedure for ova and embryos for use in Assisted Reproductive Technology (ART) so as to enhance viability and live birth rates. In particular, in some aspects, the present disclosure provides a method of selecting or screening ova and/or embryos based on Brillouin spectroscopy.

The present disclosure is at least partly based on the recognition that the Brillouin spectroscopy can be employed to quantify one or more biomechanical properties (herein also referred to as biomechanical parameters) of a reproductive cellular structure. In embodiments of the present disclosure, Brillouin spectroscopy-based methods and systems may be utilized to monitor and/or evaluate ova and/or embryos. Using the optical methods, the reproductive cellular structures may be inspected or evaluated locally, in a contactless manner, in real time, and inductively.

The Brillouin spectroscopy is based upon Brillouin scattering, in which inelastically scattered photons (typically backscattered photons) experience a frequency shift, in comparison with photons that are incident from an external light source. As discussed below, the present disclosure provides methods for determining one or more biomechanical properties of a reproductive cellular structure by measuring at least one Brillouin frequency shift associated with radiation scattered by a reproductive cellular structure in response to illuminating the reproductive cellular structure with interrogating radiation.

In-vitro fertilization (IVF) involves a complex series of procedures to help with fertility to assist conception while preventing genetic problems. FIG. 1 shows a schematic of an IVF procedure with single sperm injection via Intracytoplasmic Sperm Injection (ICSI), in which a single sperm cell is injected directly into the cytoplasm of an oocyte. In an exemplary procedure, matured eggs collected (e.g., retrieved) from ovaries may be fertilized by sperms in-vitro (i.e., in a lab setting) artificially. The fertilized egg(s), or embryo(s), which may be referred to as a proembyo, may then be transferred to a uterus.

The success rate of IVF (leading to pregnancy, for example) depends on many factors. In a study by Loendersloot et al., the authors found correlations between pregnancy and various predictors including female age, duration of subfertility, basal follicle-stimulating hormone (FSH), number of healthy oocytes retrieved, number of embryos transferred and embryos quality (Loendersloot et al., 2010; Loendersloot et al., 2014). The findings agree with other studies which concluded that embryo quality itself is an important predictor, only next to age (McKenzie et al., 2004).

Therefore, in IVF, clinicians and patients often face the challenges of selecting not only the best oocytes to fertilize but also the best embryos to transfer. Despite normal morphology and presence of chromosomes, many embryos fail during implantation process. To compensate for the failure, the clinicians typically transfer multiple embryos in over 60% of the cases ("National Summary Report," 2016). This may, however, lead to a high rate of multiple births and associated complications, and consequent risks such as adverse perinatal and maternal outcomes in addition to unanticipated financial burden (Gerris et al., 1999). Currently the most reliable methods can predict pregnancy successfully only 60-70% of the time (Forman et al., 2013) given the right age frame.

There has been much effort directed to identifying objective, quantitative, and reliable markers for developmental potential of both oocytes and embryos. In recent years, technologies such as extended culture (Forman et al., 2013), preimplantation genetic screening (PGS) (Gardner et al., 2015), and time-lapse imaging of cell cycles (VerMilyea et al., 2014) have helped identify viable embryos and reduce the incidence of multiple gestation pregnancies and have contributed to higher rates of elective single-embryo transfer. Extending the culturing of embryos to blastocysts stage was introduced for higher rate of implantation (Jones et al., 1999). However, the longer culturing time requires more time and resources, and therefore the technique is used only in a small portion of patients (Forman et al., 2013). Furthermore, the long-term risks associated are not clear, and the risk of monozygotic twins after blastocyst transfer has increased. PGS can screen embryos for chromosome abnormalities. This is based on previous findings that aneuploidy was high in spontaneous abortions (Hassold et al., 1980), and a decrease in chromosome abnormalities were observed from cleavage stage to blastocyst stage (Ata et al., 2012). Later studies confirmed that aneuploid embryos were responsible for the majority of failed IVF cycles, particularly those associated with increasing maternal age (Harton et al., 2013). Although random controlled trials confirmed that PGS can increase the success rates of implantation and live birth, it is invasive and requires highly-trained embryologists to perform trophecoderm biopsy, causing the process to be expensive and resource demanding.

Time-lapse imaging allows identification of kinetic parameters over a long period of time and helps increase the success rate of embryo selection (VerMilyea et al., 2014). In humans, various oocyte morphological parameters were discovered to correlate with embryo development and implantation potential, including zona thickness, granularity, perivitelline space and oocyte shape. Morphology-based embryo selection is one of the most widely used methods in clinical practice. However, these characteristics are highly subjective, and their predictive values are uncertain. The results have little correlation with chromosomal status (Werner et al., 2012). Some studies suggest that the embryo's fate is determined early in the developmental stage, even before fertilization (Stitzel et al., 2007; Li et al., 2010). Therefore, the pursuit of markers for oocyte/embryo quality in order to produce higher implantation and live birth rates and reduce incidences of unwanted multiple pregnancies continues to be the major topic in the IVF field.

Mechanical properties may play an important role in regulating cell fate and function at molecular level, and a cell's internal state may be reflected in its mechanical properties (Xu et al., 2012; Suresh et al., 2005). Biomechanical properties may be also critical for oocyte and embryo functions. Biomechanics of embryos and oocytes have been correlated with pregnancy in humans, and maternal age in mouse, indicating a link between mechanics and viability (Ebner et al., 2003; Murayama et al., 2008; Murayama et al., 2006).

Figure 3:
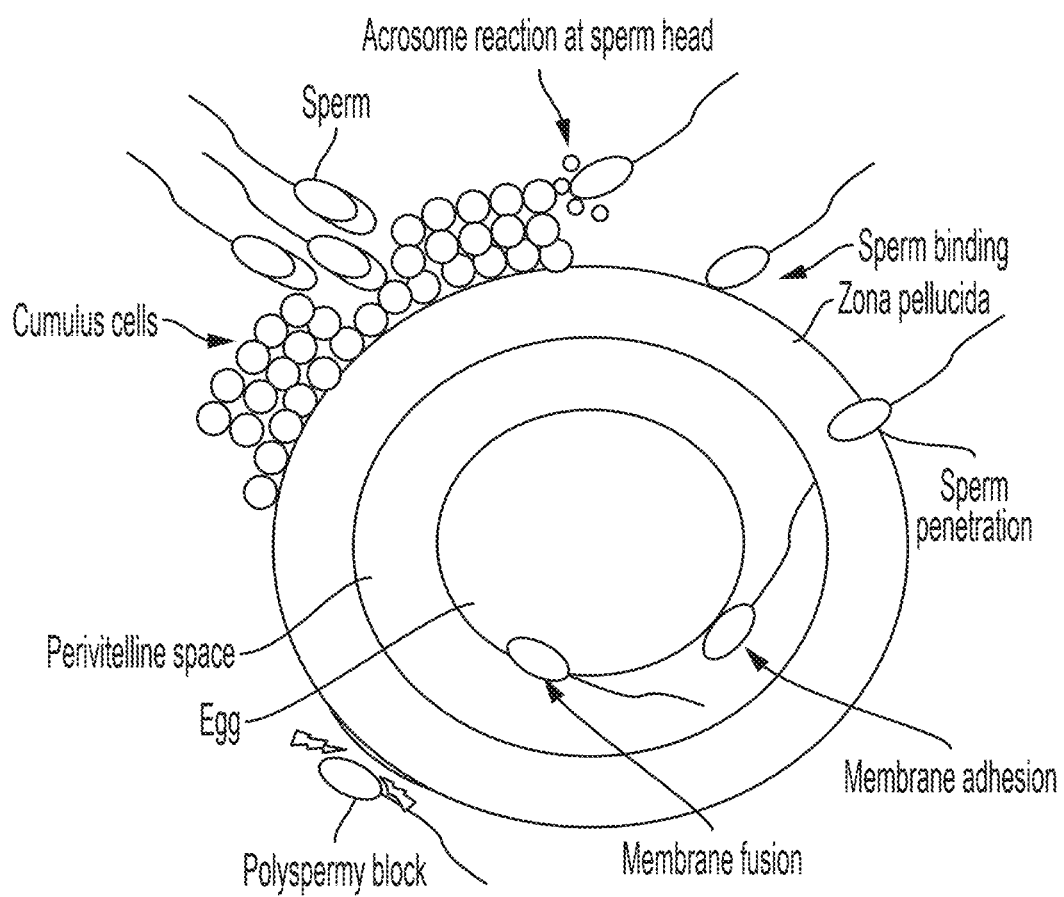
FIG. 3 shows a structure of the zygote and the fertilization procedure.

For example, the zona pellucidea, which is a network of sulfated glycoproteins, may undergo significant changes as the oocyte transitions through different stages of mitosis along with its development into a zygote as shown in FIG. 3, which shows a structure of the zygote and the fertilization procedure. The zygote may soften during maturation, which may be a mechanism to facilitate sperm penetration (Papi et al., 2010). Subsequently, the zygote may harden during fertilization. This may be due to the cortical reaction in which the cortical granules release their contents into the perivitelline space. The enzyme-mediated mechanism may be able to prevent polyspermy (Drobnis et al., 1988). Differences in zona pellucida structure and thickness have been associated with the reproductive competence of oocytes. Thinner zonas or undistinguishable inner layer may indicate lower rates of conception or blastocyst development (Ebner et al., 2010). As shown by these findings, biomechanical properties of oocytes or embryos may be effective measures for oocyte or embryo selection.

The change in the zona pellucida physical properties may be accompanied by oocyte cytoplasma viscosity during folliculogenesis and maturation (Krause et al., 2016). Some studies found correlation between higher viscosity or injection funnel persistence and poor prognoses in subsequent preimplantation development (Ebner et al., 2003).

Yanez et al. (2016) studied the potential of Zener-model-based mechanical parameters (Bausch et al., 1999) in predicting success rate of forming blastocyst in human and in mice zygote. They achieved a 90% precision, 95% specificity, and 75% sensitivity using a classifier predicting human embryo blastocyst. Accordingly, at the zygote stage, mechanical parameters may provide information about embryo viability.

An additional 48 hours in the culture may be needed to collect time-lapse cell cycle morphological parameters. The optimal combination of mechanical and cell cycle parameters may achieve a sensitivity and specificity of 90% and 91%. The authors also showed that the viable groups have significantly different transcriptomes from the non-viable groups. These results suggest that embryo potential is largely determined by the quality and maturation of the oocyte before fertilization, and also show the potential that viability of the oocytes may be predicted based on mechanical indicators.

Efforts were directed to develop techniques for the measurement of oocyte mechanical properties, using primarily microfluid approaches. Current methods of quantifying mechanical properties of oocyte and embryo may include compression, indentation, aspiration, and others.

Compression—The earliest work in this field dates back to as early as 1970s and includes studies carried by Nakamura et al. (1978) and Nemoto et al. (1980). These studies used parallel plate compression and negative pressure application via micropipette aspiration to measure parameters including cell stiffness, membrane surface tension and intracellular pressure in animal models. Nakahara et al. took time-lapse sequential mechanical measurements of zona pellucida to observe its hardening, using a force sensor (Nakahara et al., 2018). A special sensor system was designed to measure the resistance when compressing the oocyte. A group in France reported a force sensing platform similar to the one used in intra-cytoplasmic sperm injection protocol, replacing the injection pipette with a glass indenter (Gana et al., 2017). Two passive and linear-magnetic springs to measure the nano-force applied to the oocyte. They presented only preliminary results from an immature oocyte (metaphase I).

Indentation—Liu et al. reported a system to quantify oocytes resistance to externally implemented force by sub-pixel computer vision tracking (Liu et al., 2010). Using the computer vision tracking system, healthy mouse oocytes were successfully distinguished from aging-induced cellular defects.

Aspiration—Using micropipette aspiration (MPA), Evans et al. studied cortical tension, or the force in the cortex and overlying plasma membrane that serves to minimize the surface area to volume ratio (Evans et al., 2018). Yanez et al. used a modified model to evaluate the potential of Zener-model-based mechanical parameters in predicting success rate of forming blastocyst in human and mice zygote.

Other methods—Wang et al. designed a three-dimensional magnetic tweezer system for intraembryoic navigation and measurement (Wang et al., 2017). Using the magnetic tweezer system, Wang et al. investigated a mouse embryo. Intraembryonic viscosity was measured through navigating the magnetic controlled microbead inside the embryo with a known force, in an effort to make mechanical characterization of multiple locations on the inner cell mass (ICM) of the mouse embryo. In the study of Wang et al., a force was applied accurately to 5 μm magnetic beads inside the embryo. By 3D navigation of the bead(s), cytoplasm viscosity was estimated. The authors concluded that the viscosity in a mouse embryo is eight times of water viscosity. Atomic force microscopy (AFM) was used to measure mechanical properties of zona pellucida using cows and heifers oocytes (Papi et al., 2010). In this study, the researchers reported loss of zona pellucida elasticity during oocyte maturation. Andolfi et al. (2016) pushed this method to clinical studies. They analyzed oocytes from 14 patients and found that suitable metaphase II with negative outcomes showed softer outer layer zona pellucida than those achieved pregnancy. Hornick et al. used a "stiff pipette" methods to study stiffness of meiotic chromosomes (Hornick et al., 2015). They used two pipettes to precisely stretch two ends of an isolated chromosome of a mouse model to measure the resistance and observed a significant difference between the higher-age and lower-age groups, with the higher-age group showing greater force constant and potentially higher chance of aneuploidy.

While the above-listed previous studies reported some examples of biomechanical characterization, these methods require a direct contact to the tissue. Whereas some authors claimed their methods were minimally invasive (Yanez et al., 2016), their effects on later development of the embryo due to the contact required for the force impositions are still uncharacterized. In addition, some of the methods are highly invasive or destructive, and only feasible for one-time measurements in the laboratory environment for fundamental research (Gana et al., 2017; Hornick et al., 2015), but not in actual IVF procedures. In addition, these methods can only quantify biomechanical properties of the oocytes and embryos at a macro-level, not at a sub-cellular level.

Accordingly, the need for local or sub-cellular level biomechanical measurement still remains, and efforts have been made to achieve biomechanical property measurements with a higher resolution. For example, Dittman and Braunschweig combined cell-deformation with an inverse finite element method (iFEM), but this method involves simplified estimations, and only zona pellucida force-strain behavior was estimated imparting overall cell compressibility (Dittmann et al., 2018).

In view of the foregoing technical needs, the subject matter of the present disclosure provides methods and systems for contactless inspection or monitoring of reproductive cellular structures based on optical measurement of one or more of their biomechanical properties. More specifically, aspects of the present disclosure may provide an optical imaging technique for determining one or more biomechanical properties of reproductive cellular structures and optionally utilizing the biomechanical properties to select those reproductive cellular structures that are more likely to lead to successful pregnancy. Herein, the reproductive cellular structures may include embryos, zygotes, ova, oocytes, and the like. However, the reproductive cellular structures that may be characterized using the present disclosure are not limited to those explicitly disclosed herein, but may be employed to assess viability of reproductive cellular structures at any stage during the IVF. In some embodiments, the optical imaging technique may be implemented to have a sub-cellular-resolution. For example, the optical imaging technique may be based on Brillouin spectroscopy.

In some embodiments, the optical imaging system may be a Brillouin microscopic imaging system for oocytes and embryo imaging. The system may obtain three-dimensional Brillouin microscopic imaging of oocytes and embryos at sub-cellular level with ameliorated accuracy (e.g., about 10 MHz or less) and enhanced resolution (e.g., about 3 microns or less). The Brillouin microscopic imaging system may measure biomechanical properties of oocytes and embryos without negatively affecting them for subsequent development and subsequent procedure of the IVF.

In some embodiments, the biomechanical properties may be measured in the sub-cellular resolution, and may be measured in a scanning manner to obtain a spatially-resolved 2D or 3D map of the biomechanical properties of the cellular structure. In order to increase optical resolution and contrast of the images such that they are suitable to obtain the 2D or 3D scanning, one or more spatial confocal pinholes may be included in the system to block out-of-focus light in the image formation. By capturing multiple two-dimensional images at different depths in a sample (e.g., optical sectioning), the three-dimensional structure can be reconstructed with improved resolution and fidelity.

Aspects of the present disclosure also include quantifying viability of oocytes and embryos based on a Brillouin metric. The Brillouin metric may serve as a biomechanical marker for a viable reproductive cellular structure (e.g., a zygote). In addition, Brillouin measurements may be used as a metric that provides sufficient sensitivities to detect the biomechanical properties.

Further, aspects of the present disclosure include characterizing the value of Brillouin measurements on zygotes to predict implementation and live birth success in animals or in humans. By way of example, a metric derived based on Brillouin spectroscopy in accordance with the present disclosure may be used to predict the likelihood that the use of oocytes and embryos would lead to successful live birth. In other words, Brillouin measurements of one or more biomechanical properties of oocytes and/or embryos may serve as a biomechanical marker to predict live birth.

By way of example and as discussed in more detail below, in some embodiments, the modulus of elasticity obtained via analysis of Brillouin scattered radiation in accordance with the present disclosure can be used to assess the stiffness or firmness of oocytes, zygotes and/or embryos and the stiffness or firmness of the oocytes, zygotes and/or embryos may be correlated with successful pregnancy. In some such embodiments, biomechanical measurements may predict embryo potentials at the zygote stage in animals or in humans.

According to related aspects of the present disclosure, the present disclosure may result in significant enhancement of clinical management of IVF. For example, Brillouin-based biomechanics metrics may be utilized to make better decisions on the selection of viable oocytes. Oocyte screening for donor ova may be more reliably performed to identify viable oocytes, which may enhance the fertilization process. In addition, quantitative biomechanical assessment of oocyte before fertilization and embryos after fertilization may further improve the viability and live birth rates, and may reduce the incidence of unwanted multiple pregnancies. The advanced Brillouin technology and optical instrumentation may generally benefit the fertility clinic by advancing fundamental understanding of the mechanical or biomechanical properties of oocytes and embryos. Furthermore, the Brillouin measurements of oocytes and embryos may lead to more active exploration of biomechanics in the ART field.

Hereinbelow, a description of a typical IVF procedure, and the significance of subject matter of the present disclosure during the IVF procedure will be explained. In a typical IVF, embryos may be grown under a controlled laboratory environment for 2 to 3 days after fertilization. The grown embryos may then be transferred to a woman's uterus.

Figure 2:
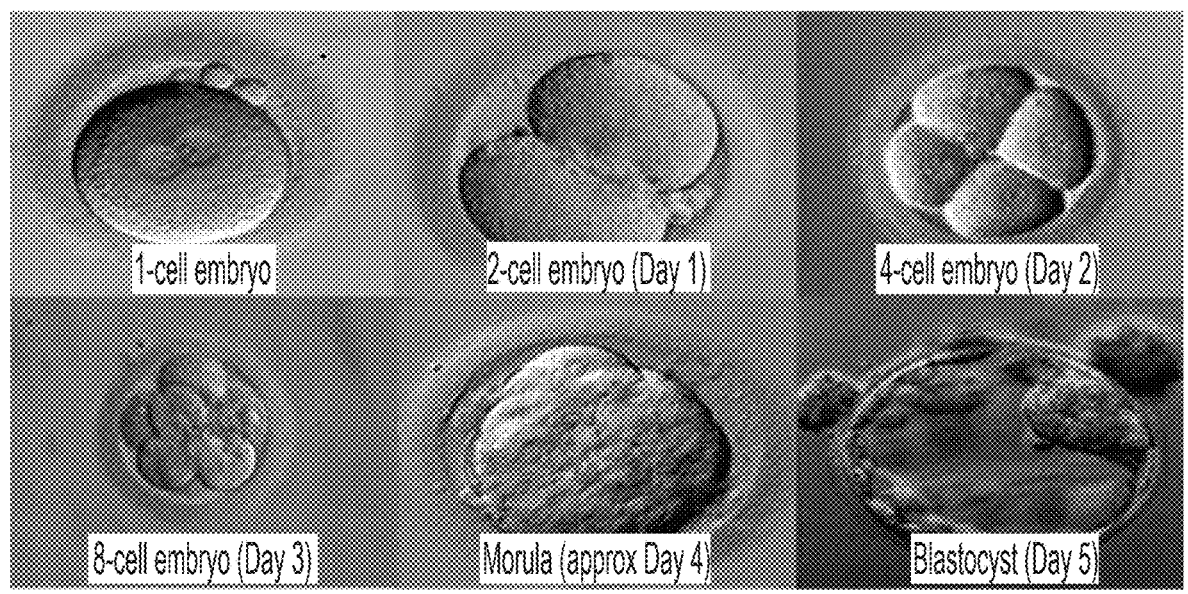
FIG. 2 shows preimplantation development of human embryos.

To increase success rate, the embryos may be cultured in-vitro until a later stage at which the embryos are ready for implantation. FIG. 2 shows preimplantation development of a human embryo. About 90 minutes after fertilization, the zygote may divide into two cells and enter the two-cell blastomere state. It may be considered the earliest mitotic product of the fertilized oocyte. These mitotic divisions may continue and result in a grouping of cells called blastomeres. When the zygote contains 16 to 32 cells, it may be referred to as a morula. The division of blastomeres from the zygote may allow the single fertile cell to continue to cleave and differentiate until a blastocyst form.

There are a number advantages when the embryo selection methods are noninvasive, inexpensive, easy to use, strongly predictive for viability, and applicable to both oocyte and embryos. Hence, in some embodiments, the present disclosure provides biomechanical assessment, via Brillouin microscopy, of oocytes and embryos for embryo selection.

As noted above, the subject matter of the present disclosure provides methods for non-invasive measurement of one or more biomechanical properties of reproductive cellular structures. In particular, the methods according to the present disclosure may use Brillouin spectroscopy for non-invasive and non-contact characterization of biomechanical properties of reproductive cellular structures, such as their modulus of elasticity and/or viscosity. Therefore, Brillouin spectroscopy-based methods and systems of the present disclosure may allow non-invasive inspection of ova and/or embryos locally (e.g., at a sub-cellular resolution) in real time, and inductively.

In Brillouin spectroscopy of reproductive cellular structures according to the present disclosure, a photon incident on a reproductive cellular structure may be scattered via interaction with an acoustic phonon to produce a photon at a slightly lower or higher energy. The energy (and hence frequency) shift of the scattered photon is thus related to the energy of the acoustic phonon, which may in turn be related to the modulus of elasticity of the reproductive cellular structure. Hence, as discussed in more detail below, the Brillouin frequency shift may be utilized to obtain an estimate of the modulus of elasticity of the reproductive cellular structure (e.g., an average value of a plurality of sub-cellular values).

Figure 4:
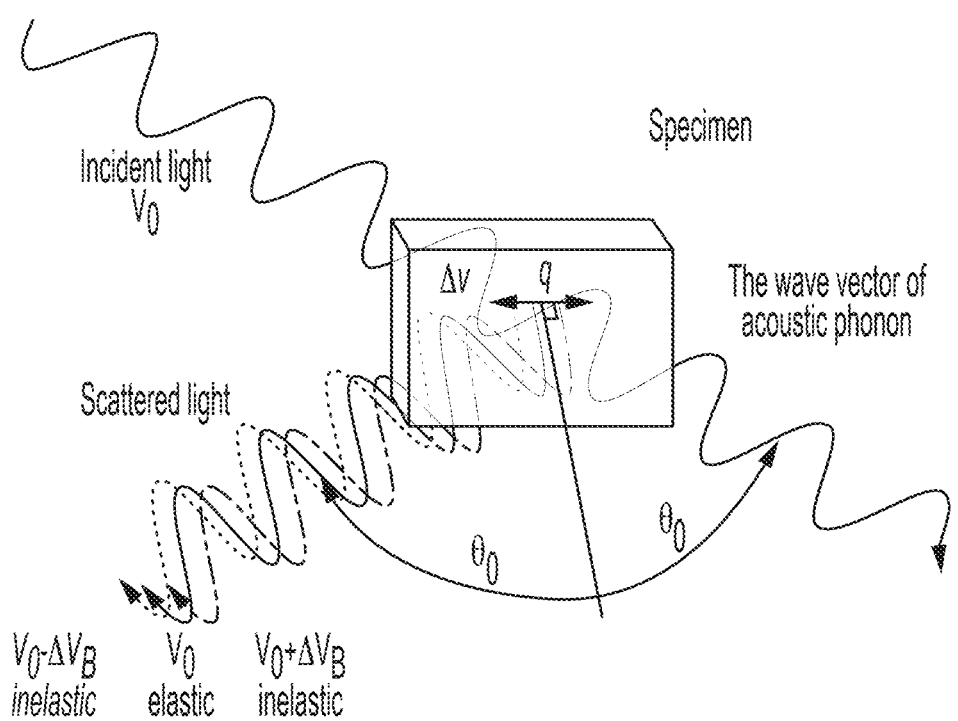
FIG. 4 schematically illustrates Brillouin scattering measurement according to an exemplary embodiment of the present disclosure.

As shown in FIG. 4, a specimen (e.g., a reproductive cellular structure) may be illuminated with an incident light beam having a central optical frequency of $v_0$ (shown in green). Upon interacting with the specimen, the light may be divided into an elastic scattered portion and an inelastically scattered portion corresponding to Brillouin scattered radiation. The undisturbed, elastic scattered portion, having the frequency of $v_0$, may be eliminated, e.g., using one or more optical filters, to reveal the inelastically scattered Brillouin components that are shown in blue and orange colors (or in dashed lines), having the frequency of $v_0+\Delta v_B$ and $v_0-\Delta v_B$, respectively. The frequency shift component $\Delta v_B$ may be measured using a spectrometer. The resulting frequency shift of the incident and the scattered light (e.g., laser beams) may define the Brillouin spectrum, which directly relates to the longitudinal elastic modulus at the probed location of the specimen. Depending on the frequency of the light source, the measurement resolution may be tuned. Moreover, the spatial distribution of mechanical properties may be mapped out across the specimen using Brillouin imaging.

In some embodiments, the radiation source can be a laser providing radiation having a vacuum wavelength between about 400 nm and about 800 nm, and a radiation output power between in a range of about 1 mW and about 100 mW. By way of example, the laser may have a wavelength of about 400 nm, about 425 nm, about 450 nm, about 475 nm (blue), about 500 nm, about 525 nm (green), about 550 nm, about 575 nm, about 600 nm, about 625 nm, about 650 nm, about 675 nm, about 700 nm (red), about 725 nm, about 750 nm, about 775 nm, or about 780. By way of example, the laser may have a power of about 1 mW, about 2.5 mW, about 5 mW, about 7.5 mW, about 10 mW, about 20 mW, about 30 mW, about 40 mW, about 50 mW, about 75 mW, or about 100 mW.

The Brillouin scattering shift $\Delta v_B$ measured in accordance with the method of the present disclosure may be between about 5 GHz and about 15 GHz. By way of example, the Brillouin scattering component $\Delta v_B$ may be about 5 GHz, about 6 GHz, about 7 GHz, about 8 GHz, about 9 GHz, about 10 GHz, about 11 GHz, about 12 GHz, about 13 GHz, about 14 GHz, or about 15 GHz, depending, for example, on the reproductive cellular structure under investigation (e.g., oocytes or embryos).

According to the present disclosure, the Brillouin frequency shift may be measured with a minimum detection resolution of about 0.05 GHz (i.e., 50 MHz) or less. By way of example, the detection resolution may be about 10 MHz or less. Due to such a level of accuracy, the optical measurement techniques according to the present disclosure can provide reliable measurements that can be applied for human cells.

The measured Brillouin scattering shift $\Delta v_B$ may be correlated to (high-frequency) longitudinal storage modulus (also referred to as "modulus of elasticity") M', which is a ratio of a stress in the longitudinal direction to a strain in the longitudinal direction, by the following formula.

$$\Delta v_B = \frac{2n}{\lambda}\sqrt{\frac{M'}{\rho}}\sin\left(\frac{\theta}{2}\right)$$

where n is the refractive index of medium, e.g., a reproductive cell; $\lambda$ the vacuum wavelength of the source light; p the density of the medium, e.g., a reproductive cell; and $\theta$ is the angle between the incident light and the scattered light. For backward scattering, $\theta$ is approximately 180 deg, and sin ($\theta$/2) becomes approximately 1. Accordingly, the longitudinal modulus M' may be obtained by the following formula.

$$M' = \rho\left(\frac{\lambda}{2n}\right)^2 \Delta v_B^2$$

In turn, the longitudinal storage modulus M' may be correlated to Young's modulus E' by the following formula.

$$\log M' = \alpha \log E' + b$$

where a and b are calibration coefficients.

To obtain a complex longitudinal modulus M* for a complete viscoelastic constitutive model, the Brillouin peaks linewidth $\Gamma_B$ may also be measured. Similar to the storage modulus, a longitudinal loss modulus (also referred to as "modulus of viscosity") M" may be obtained from the following formula.

$$M'' = \rho\left(\frac{\lambda}{2n}\right)^2 \Delta v_B \Gamma_B$$

For the viscoelastic constitutive model, the complex longitudinal modulus M* may be expressed as:

$$M^* = M' + i\,M''\text{ wherein } i \text{ denotes a unit imaginary number which satisfies } i^2 = -1$$

where M' is the storage modulus, and M" is the loss modulus. The storage modulus measures the stored energy (elastic portion) and the loss modulus measures the energy dissipated as heat, which quantifies the viscous portion of the complex longitudinal modulus. Spontaneous Brillouin light scattering arises from the interaction of photons with acoustic phonons. The interaction can be understood as scattering of light by the modulation of refractive index in the medium, caused by propagating pressure waves of thermodynamic fluctuations. Because the fluctuations are stochastic, the waves have a white spectrum (i.e. all frequency components) and propagate in all directions at the speed of acoustic waves. The light scattered from phase-matching acoustic waves experience a Doppler frequency shift with a magnitude equal to the frequency of the mechanical waves typically ranging from 5 to 10 GHz. The frequency can be readily measured with Brillouin spectroscopy. Throughout a series of derivation procedure, final form of constitutive formula can be expressed as, $$M^* = \rho\left(\frac{\lambda}{2n}\right)^2 \Delta v_B^2 + i\rho\left(\frac{\lambda}{2n}\right)^2 \Delta v_B \Gamma_B$$

As described above, the storage modulus for elastic portion is the function of Brillouin frequency shift ($\Delta v_B^2$), and the loss modulus for viscous portion is the function of Brillouin frequency shift and Brillouin peaks linewidth ($\Delta_{\nu_B}\Gamma_B$). Both $\Delta_{\nu_B}$ and $\Gamma_B$ can be measured via Brillouin microscopic measurements and followed numerical analysis. Brillouin frequency shift and peaks linewidth measurement using the Brillouin spectrometer may be impacted by the optical resolution on the spectrum. Accurate measurement of those two variables can be made by deconvolving the spectrum using the measured system response using the two virtually imaged phase array (VIPA) spectrometer.

As described above, a spatially-resolved modulus of elasticity map may be obtained via 2D and/or 3D scanning of the incident radiation and detecting the Brillouin scattered radiation from the scanned locations. Using the spatially-resolved and/or representative (e.g., overall or global) modulus of elasticity, a viability index of an oocyte or an embryo may be evaluated. Further, in some embodiments, the Brillouin-based viability index may be applied universally. In other embodiments, the Brillouin-based viability index may be evaluated in conjunction with personal factors, such as ethnicity, medical history, etc.

Hereinbelow, exemplary embodiments of the methods and systems for measuring biomechanical properties of reproductive cellular structures and using the measured biomechanical properties to identify, select, or screen viable reproductive cellular structures according to the present disclosure will be described.

Figure 5:
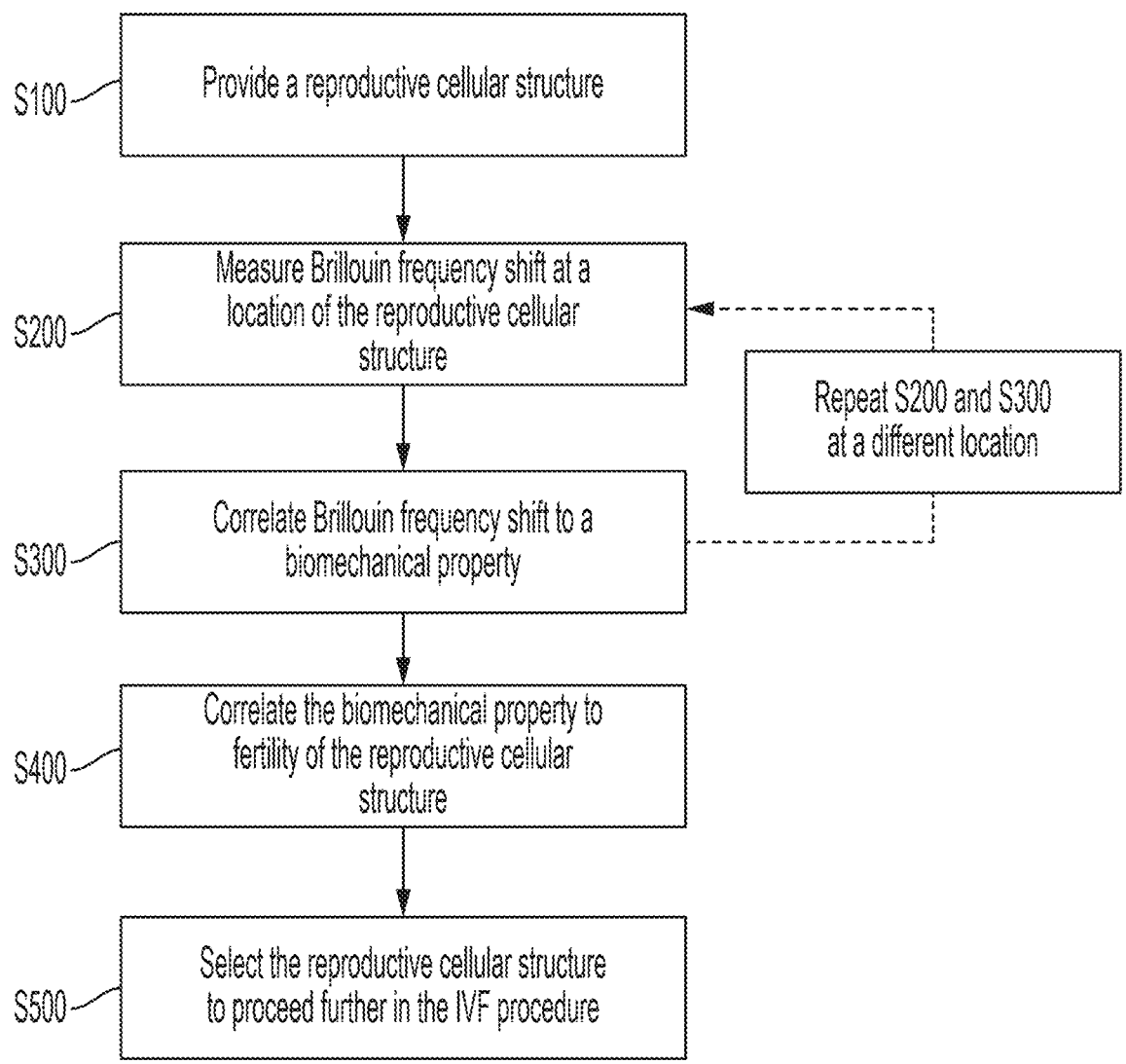
FIG. 5 shows a flowchart for optically characterizing biomechanical properties of reproductive cellular structures according to an exemplary embodiment of the present disclosure.
Figure 6:
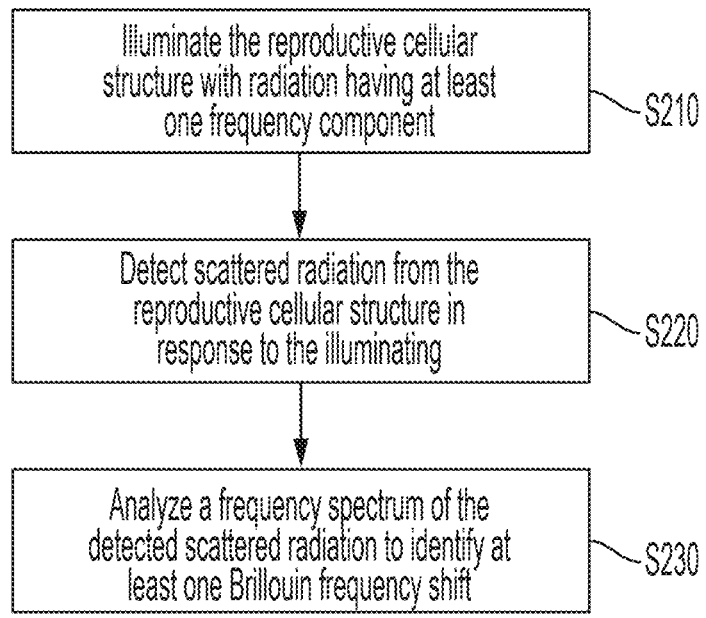
FIG. 6 shows a flowchart for measuring Brillouin frequency shift at a location of the reproductive cellular structure.

FIG. 5 shows a flowchart for optically inspecting or characterizing biomechanical properties of reproductive cellular structures according to an exemplary embodiment of the present disclosure. The method of contactless inspection of reproductive cellular structures may include obtaining (e.g., collecting) a reproductive cellular structure (S100), and measuring Brillouin frequency shift at a location of the reproductive cellular structure using an optical imaging technique (S200). Referring to FIG. 6, the measurement of the Brillouin frequency shift (S200) may include illuminating the reproductive cellular structure with radiation (S210), detecting scattered (e.g., backscattered) radiation (S220), and analyzing the detected radiation to identify at least one Brillouin frequency shift, e.g., using a spectrometer (S230).

Subsequently, the measured Brillouin spectrum may be correlated to a biomechanical property of the reproductive cellular structure (S300). In some embodiments, the steps S200 and S300 may be repeated to obtain a 2D or 3D map of the biomechanical properties across the reproductive cellular structure. The biomechanical property may be further correlated to fertility of the reproductive cellular structure (S400). Based on the determined fertility, the reproductive cellular structure may be identified, selected, or screened for further procedure in the IVF (S500).

The step of measuring Brillouin frequency shift at a location of the reproductive cellular structure (S200) is described in more detail with reference to FIG. 6. Referring to FIG. 6, the reproductive cellular structure may be illuminated with radiation having at least one desired frequency component (S210). In some embodiments, the illuminating radiation may be laser radiation. In turn, at least a portion of radiation scattered from the reproductive cellular structure may be detected (S220). Subsequently, a frequency spectrum of the detected scattered radiation may be analyzed to identify at least one Brillouin frequency shift (e.g., down-shifted or upshifted frequency component) in the frequency spectrum (S230). In some embodiments, the radiation that is elastically scattered from the reproductive cellular structure may be filtered out to facilitate detection of the Brillouin frequency shift.

In some embodiments, the step of providing a reproductive cellular structure (S100) may further include fixating the reproductive cellular structure. By way of example, the reproductive cellular structure may be fixated for the optical observation via mechanical holding, electromagnetic holding, or fluid-dynamic holding. In other embodiments, the sample-container and/or the optical components of the Brillouin spectrometer may be moved such that the observed cell is positioned at the optimal location for observation. By way of example, a software algorithm may be implemented to move the sample-container and/or the optical components of the Brillouin spectrometer based on image-recognition techniques. In such embodiments, the image-recognition may be based on a neutral-network algorithm to identify the cell and its extent. Once identified, the sample may be maintained at the center of the view using the motorized stage, or the scanner settings may be dynamically updated based on the sample location. The image-recognition technique can speed up the initial localization of the sample as the first step of the measurement.

The reproductive cellular structure to be measured may include an embryo, a zygote, an ovum, an oocyte, or the like. In some implementations, the biomechanical properties of oocytes may be measured to select the most viable oocyte(s) to be fertilized with a male gamete among a plurality of oocytes. In some implementations, the biomechanical properties of embryos may be measured to select the most viable embryo(s) to transfer to a uterus. However, the optical inspection according to the present disclosure is not limited to the selection of oocytes and embryos, but may also be applied during various stages of the in-vitro fertilization.

The fertility of the reproductive cellular structure may be indicated by viability, live-birth rate, developmental potential, and the like. However, the fertility of the reproductive cellular structure is not limited thereto, and it may point to various measures that indicate the probability of successful conception. In some embodiments, the fertility may be quantified as a viability index. For example, when the measured Brillouin frequency shift falls between about 5.0 GHz and about 6.2 GHz, the reproductive cellular may be determined to possess high viability for live-birth, and thus the viability index may be evaluated to be the highest. The viability index may also reflect a series of measurements, e.g., based on the Brillouin spectrometry described above, taken over a timespan. The viability index may further reflect other metrics, such as chemical measurements, as well as the Brillouin spectrometry.

As described above, using the spatially-resolved and/or representative (e.g., overall) modulus of elasticity, the oocyte exhibiting the highest viability index (e.g., falling in a predetermined Young's modulus range or in a predetermined Brillouin scattering component range) may be selected for proceeding with sperm injection. By way of example, the Young's modulus range that leads to likelihood of viability may be between about 2 GPa and about 6 GPa, which may correspond to the Brillouin frequency shift of between about 5 GHz and about 15 GHz. In some embodiments, the embryo exhibiting the highest viability index (e.g., falling in a predetermined Young's modulus range or in a predetermined Brillouin scattering component range) may be selected for proceeding with implantation.

Further, in some embodiments, the Brillouin-based viability index may be applied solely based on the measured biomechanical properties. In other embodiments, the Brillouin-based viability index may be evaluated in conjunction with personal factors such as the parents' age, ethnicity, medical condition/history, etc. By way of example, in some embodiments, conventional metrics (e.g., parent's age, ethnicity, medical condition/history, etc.) can be used to narrow down the oocyte to a few and then Brillouin scattering measurements according to the present disclosure can be employed to select an oocyte from among those initially selected via conventional parameters for fertilization.

Figure 7:
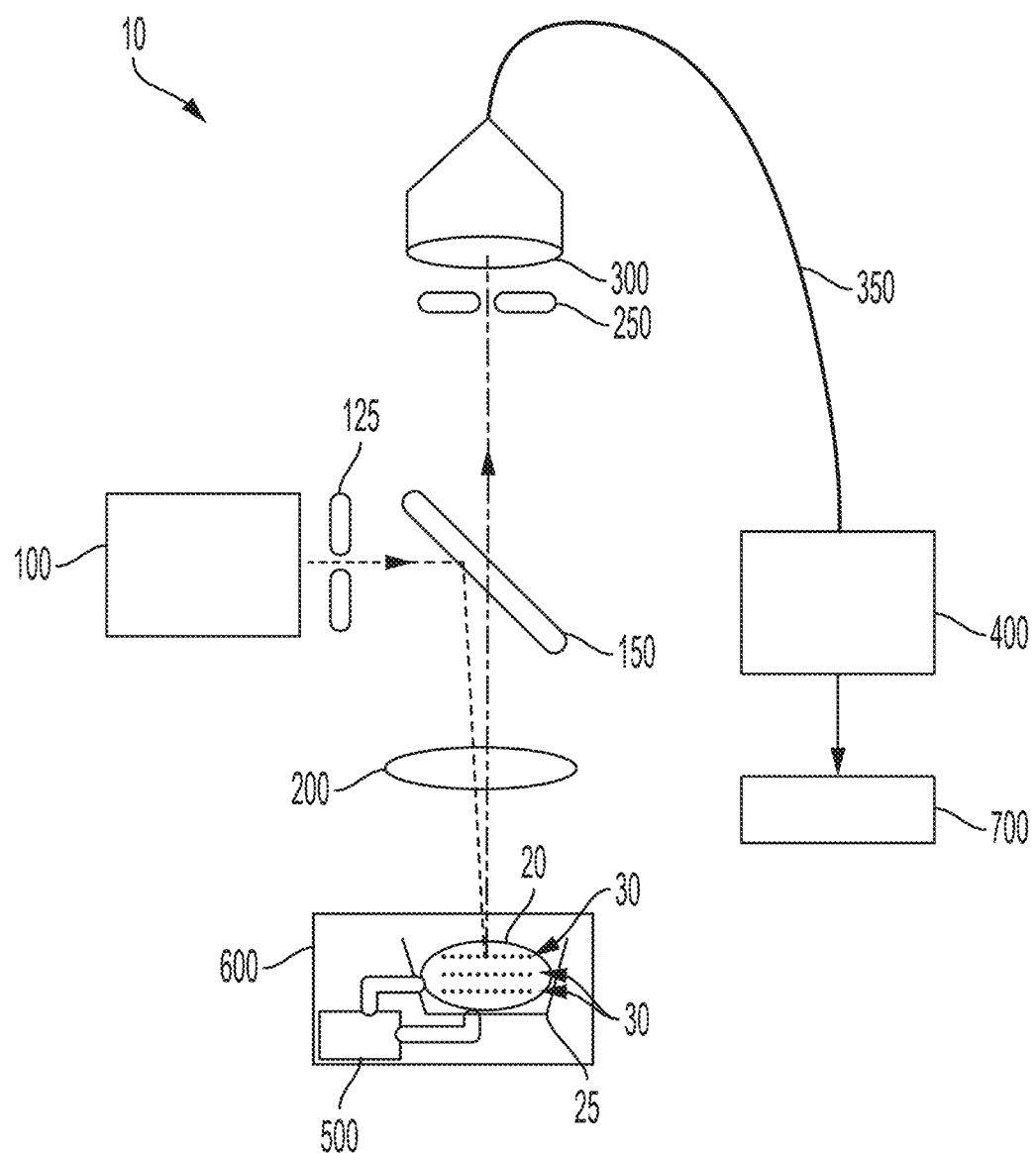
FIG. 7 illustrates a system for optically characterizing biomechanical properties of reproductive cellular structures according to an exemplary embodiment of the present disclosure.

FIG. 7 illustrates a system 10 for optically inspecting and/or characterizing biomechanical properties of reproductive cellular structures according to an exemplary embodiment of the present disclosure. As shown in FIG. 7, the system 10 for optical inspection of reproductive cellular structures according to an exemplary embodiment of the present disclosure may include a light emitting source (e.g., a laser) 100 that generates radiation for illuminating a sample 20 (e.g., a reproductive cellular structure). The generated radiation may be reflected by a dichroic mirror 150 onto an optic 200 (which is in the form of an objective lens in this embodiment), which may in turn focus the radiation onto the sample 20. A light receiving component 300 may receive at least a portion of the light scattered by the reproductive cellular structure, the received light may be transmitted through an optical fiber 350, and a spectrometer 400 may measure a frequency shift component of the scattered light.

In some embodiments, to block the out-of-focus light, a pinhole 250 may be disposed in front of (i.e., upstream) of the light receiving component 300. The system 10 may further include another pinhole 125 in front of (i.e., downstream) of the light emitting source 100. Due to the pinholes 250 and/or 125, the system 10 can adjust focal planes 30, and therefore, may provide optical sectioning and vertical scanning for the 2D or 3D scanning. In some embodiments, using the confocal system, the vertical scanning may be obtained with a resolution below about 5 µm. By way of example, the vertical scanning resolution may be about 5 µm, about 4 µm, about 3 µm, about 2 µm, or about 1 µm. In some embodiments, a single-mode optical fiber may be employed, although in other embodiments, multi-mode optical fibers may also be used as the optical fiber 350. Due to the small core diameter thereof, the single-mode optical fiber may inherently function as a pinhole, and therefore may combine the functions of the pinhole 250, the light receiving component 300, and the optical fiber 350.

In an analyzer 700, the measured frequency shift component may be correlated to a biomechanical property of the reproductive cellular structure, and subsequently, the biomechanical property of the reproductive cellular structure may be correlated to fertility of the reproductive cellular structure. The analyzer 700 can be implemented in hardware, software, and/or firmware in a manner known in the art as informed by the present disclosure. For example, the analyzer can include a processor and one or more memory modules that are in communication with the processor. Instructions according to the present disclosure for correlating one or more measured biomechanical properties of a reproductive cellular structure to the likelihood that it can lead to a successful IVF outcome can be stored in a memory module of the analyzer to be accessed by the processor during runtime.

In order to characterize the sample 20 in a scanning manner, the system may further include one or more actuators 500. In FIG. 7, the actuator 500 is shown to be coupled to a sample holder 25 that contains the sample 20 and translate the sample holder 25 on the horizontal plane relative to a table 600 so as to illuminate various locations within the sample 20 with the interrogating radiation. In use, the sample holder 25 may be various types of petri dishes that are used in embryology workflow, and the actuator 500 and the table 600 may be designed to accommodate various types of the sample holder 25.

However, the present disclosure is not limited to such a configuration, and the actuator 500 may translate the optical components to create a relative movement between the optical components and the sample 20 in order to illuminate different portions of the sample. In some embodiments, the actuator 500 may move a position and/or orientation of the objective lens 200 to perform the scanning. In some embodiments, by causing a relative horizontal movement between the sample 20 and the optical components of the system 10, the horizontal scanning may be obtained with a resolution below about 5 µm. By way of example, the horizontal scanning resolution may be about 5 µm, about 4 µm, about 3 µm, about 2 µm, or about 1 µm.

As described above, the system may further include a device for moving the sample holder 25 relative to the table 600 and/or the optical components (e.g., the objective lens 200) relative to the sample 20 such that the cellular structure is positioned at the optimal location for observation. In some such embodiments, the actuator may adjust the relative position of the cellular structure based on, for example, image-recognition techniques.

The measured frequency shift component may correspond to Brillouin spectrum. Further, the biomechanical properties may include a modulus of elasticity or a modulus of viscosity of the reproductive cellular structure. As noted above, the reproductive cellular structure characterized with a system according to the present disclosure may include an embryo, a zygote, an ovum, an oocyte, or the like. In order for the system to more effectively characterize the reproductive cellular structure, the optical system may have a sub-cellular resolution. Accordingly, the biomechanical property of a particular location or spot may be measured, and the system may inspect the reproductive cellular structure in a scanning manner to allow the biomechanical properties thereof to be mapped out across the reproductive cellular structure. In some embodiments, a representative spot measurement of biomechanical properties may be utilized to evaluate a reproductive cellular structure, or a global biomechanical property (e.g., one obtained by spatially averaging the local biomechanical properties) may be utilized.

As set forth herein, the subject matter of the present disclosure provides a capability to inspect reproductive cellular structures such as oocytes and embryos by optically characterizing one or more biomechanical properties thereof such as a modulus of elasticity and a modulus of viscosity. Therefore, the reproductive cellular structures may be inspected non-invasively and in a contactless manner, to select a most viable specimen to further proceed in the IVF procedure, potentially improving the probability of successful IVF.

Hereinabove, although the present disclosure is described by specific matters such as concrete components, and the like, the exemplary embodiments and the drawings are provided merely for assisting in the entire understanding of the present disclosure. Therefore, the present disclosure is not limited to the exemplary embodiments described herein. Various modifications and changes can be made by a person of ordinary skill in the art to which the present disclosure pertains. The spirit of the present disclosure should not be limited to the above-described exemplary embodiments, and the following claims as well as all technical spirits modified equally or equivalently to the claims should be interpreted to fall within the scope and spirit of the disclosure.

All publications referenced hereinabove are incorporated by reference in their entireties. A list of references cited in the present disclosure are as follows:

[1] A. Fetteers, "Sperm Counts Continue to Fall," 2018.
[2] C. Huang et al., "Decline in semen quality among 30,636 young Chinese men from 2001 to 2015," Fertil. Steril., 2017.
[3] P. Sengupta, U. Nwagha, S. Dutta, E. Krajewska-Kulak, and E. Izuka, "Evidence for decreasing sperm count in African population from 1965 to 2015," Afr. Health Sci., 2017.
[4] N. E. Skakkebaek et al., "Populations, decreasing fertility, and reproductive health," Lancet, vol. 393, no. 10180, pp. 1500-1501, 2019.
[5] BCC, "US Fertility Clinics Market," January, 2018.
[6] Loendersloot et al. "Predictive factors in in vitro fertilization (IVF): a systematic review and meta-analysis," Hum Reprod Update, vol. 16, no. 6, 577-89, 2010.
[7] Loendersloot et al. "Prediction models in in vitro fertilization; where are we? A mini review," J Adv Res., vol. 5, no. 3, 295-301, 2014.
[8] McKenzie et al. "Human cumulus granulosa cell gene expression: a predictor of fertilization and embryo selection in women undergoing IVF," Human Reproduction vol. 19, no. 12, pp. 2869-2874, 2004
[9] "National Summary Report," 2016. [Online]. Available: https://www.sartcorsonline.com/rptCSR_PublicMultYear.aspx?ClinicPKID %02016.
[10] J. Gerris and J. L. H. Evers, "Prevention of twin pregnancy after in vitro fertilization/intracytoplasmic sperm injection based on strict embryo criteria: A prospective randomized trial," Evidence-based Obstet. Gynecol., 1999.
[11] E. J. Forman et al., "In vitro fertilization with single euploid blastocyst transfer: A randomized controlled trial," Fertil. Steril., 2013.
[12] D. K. Gardner, M. Meseguer, C. Rubio, and N. R. Treff, "Diagnosis of human preimplantation embryo viability," Hum. Reprod. Update, 2015.
[13] M. D. VerMilyea et al., "Computer-automated time-lapse analysis test results correlate to clinical pregnancy and embryo implantation: A prospective, blinded, multi-center study," Human Reproduction. 2014.
[14] G. M. Jones and A. O. Trounson, "Blastocyst stage transfer: Pitfalls and benefits the benefits of extended culture," Hum. Reprod., vol. 14, no. 6, pp. 1405-1408, 1999.
[15] T. Hassold et al., "A cytogenetic study of 1000 spontaneous abortions," Ann. Hum. Genet., 1980.
[16] B. Ata et al., "Array CGH analysis shows that aneuploidy is not related to the number of embryos generated," Reprod. Biomed. Online, 2012.
[17] G. L. Harton et al., "Diminished effect of maternal age on implantation after preimplantation genetic diagnosis with array comparative genomic hybridization," Fertil. Steril., vol. 100, no. 6, pp. 1695-1703, 2013.
[18] M. Werner, A. Reh, J. Grifo, and M. A. Perle, "Characteristics of chromosomal abnormalities diagnosed after spontaneous abortions in an infertile population," J. Assist. Reprod. Genet., 2012.
[19] M. L. Stitzel and G. Seydoux, "Regulation of the oocyte-to-zygote transition," Science. 2007.
[20] L. Li, P. Zheng, and J. Dean, "Maternal control of early mouse development," Development. 2010.
[21] W. Xu, R. Mezencev, B. Kim, L. Wang, J. McDonald, and T. Sulchek, "Cell Stiffness Is a Biomarker of the Metastatic Potential of Ovarian Cancer Cells," PLoS One, 2012.
[22] S. Suresh et al., "Connections between single-cell biomechanics and human disease states: Gastrointestinal cancer and malaria," Acta Biomater., 2005.
[23] T. Ebner, M. Moser, M. Sommergruber, M. Puchner, R. Wiesinger, and G. Tews, "Developmental competence of oocytes showing increased cytoplasmic viscosity," Hum. Reprod., 2003.
[24] Y. Murayama et al., "Elasticity Measurement of Zona Pellucida Using a Micro Tactile Sensor to Evaluate Embryo Quality," J. Mamm. Ova Res., 2008.
[25] Y. Murayama et al., "Mouse zona pellucida dynamically changes its elasticity during oocyte maturation, fertilization and early embryo development.," Hum. cell Off. J. Hum. Cell Res. Soc., 2006.
[26] M. Papi et al., "Mechanical properties of zona pellucida hardening," Eur. Biophys. J., 2010.
[27] E. Z. Drobnis, J. B. Andrew, and D. F. Katz, "Biophysical properties of the zona pellucida measured by capillary suction: Is zona hardening a mechanical phenomenon?," J. Exp. Zool., 1988.
[28] T. Ebner et al., "Automatic user-independent zona pellucida imaging at the oocyte stage allows for the prediction of preimplantation development," Fertil. Steril., 2010.
[29] I. Krause et al., "Characterization of the injection funnel during intracytoplasmic sperm injection reflects cytoplasmic maturity of the oocyte," Fertil. Steril., 2016.
[30] N. Kawano, K. Yoshida, Y. Harada, N. Onami, Y. Takezawa, and K. Miyado, "Roles of CD9 and CD9-Containing Exosomes in Sperm-Egg Membrane Fusion," J. Mamm. Ova Res., 2010.
[31] L. Z. Yanez, J. Han, B. B. Behr, R. A. R. Pera, and D. B. Camarillo, "Human oocyte developmental potential is predicted by mechanical properties within hours after fertilization," Nat. Commun., 2016.
[32] A. R. Bausch, W. Möller, and E. Sackmann, "Measurement of local viscoelasticity and forces in living cells by magnetic tweezers," Biophys. J., 1999.
[33] S. Nakamura and Y. Hiramoto, "Mechanical Properties of the Cell Surface in Starfish Eggs," Dev. Growth Differ., 1978.
[34] S.-I Nemoto, M. Yoneda, and I. Uemura, "Marked Decrease in the Rigidity of Starfish Oocytes Induced by 1-Methyladenine," Dev. Growth Differ., 1980.
[35] K. Nakahara, S. Sakuma, M. Kawahara, M. Takahashi, and F. Arai, "Time-Lapse Mechanical Characterization of Zona Pellucida Using a Cell Carrier Chip," J. Microelectromechanical Syst., 2018.
[36] R. Gana et al., "A novel force sensing platform using passive magnetic springs for mechanical characterisation of human oocytes," Sensors Actuators, A Phys., vol. 262, pp. 114-122, 2017.
[37] X. Liu, R. Fernandes, A. Jurisicova, R. F. Casper, and Y. Sun, "In situ mechanical characterization of mouse oocytes using a cell holding device," Lab Chip, 2010.
[38] J. P. Evans and D. N. Robinson, "Micropipette Aspiration of Oocytes to Assess Cortical Tension," in Methods in Molecular Biology, 2018.
[39] X. Wang et al., "Three-dimensional robotic control of a 5-micrometer magnetic bead for intra-embryonic navigation and measurement," in Proceedings—IEEE International Conference on Robotics and Automation, 2017.

[40] M. Papi et al., "Mechanical properties of zona pellucida hardening," Eur. Biophys. J., vol. 39, no. 6, pp. 987-992, 2010.

[41] L. Andolfi et al., "Investigating the mechanical properties of zona pellucida of whole human oocytes by atomic force spectroscopy," Integr. Biol. (United Kingdom), vol. 8, no. 8, pp. 886-893, 2016.

[42] J. E. Hornick, F. E. Duncan, M. Sun, R. Kawamura, J. F. Marko, and T. K. Woodruff, "Age-associated alterations in the micromechanical properties of chromosomes in the mammalian egg," J. Assist. Reprod. Genet., vol. 32, no. 5, pp. 765-769, 2015.

[43] J. Dittmann, A. Dietzel, and M. Böl, "Mechanical characterisation of oocytes—The influence of sample geometry on parameter identification," J. Mech. Behav. Biomed. Mater., 2018.

[44] G. Scarcelli, R. Pineda, and S. H. Yun, "Brillouin optical microscopy for corneal biomechanics," Investig. Ophthalmol. Vis. Sci., vol. 53, no. 1, pp. 185-190, 2012.

[45] P. Shao, R. D. Stulting, D. A. Woolfson Jonathan M. Chernyak, and S.-H. Yun, "Brillouin microscopy of human corneas before and after epi-on cross-linking," J. Cataract Refract. Surg., vol. in prep.

[46] G. Antonacci et al., "Quantification of plaque stiffness by Brillouin microscopy in experimental thin cap fibroatheroma," J. R. Soc. Interface, 2015.

[47] J. Zhang et al., "Tissue biomechanics during cranial neural tube closure measured by Brillouin microscopy and optical coherence tomography," Birth Defects Res., 2019.

[48] C. Conrad, K. M. Gray, K. M. Stroka, I. Rizvi, and G. Scarcelli, "Mechanical Characterization of 3D Ovarian Cancer Nodules Using Brillouin Confocal Microscopy," Cell. Mol. Bioeng., 2019.

What is claimed is:

1. A method of measuring at least one biomechanical property of a reproductive cellular structure, the method comprising:
illuminating the reproductive cellular structure with radiation;
detecting at least a portion of radiation scattered from the illuminated reproductive cellular structure;
analyzing a frequency spectrum of the detected scattered radiation to identify at least one Brillouin frequency shift in the frequency spectrum;
obtaining a modulus of elasticity of at least a portion of the reproductive cellular structure based on the at least one Brillouin frequency shift; and
determining viability of the reproductive cellular structure based on the modulus of elasticity.

2. The method of claim 1, further comprising obtaining a modulus of viscosity of at least a portion of the reproductive cellular structure.

3. The method of claim 2, further comprising:
deriving the modulus of elasticity M' using the following formula:

$$M' = \rho\left(\frac{\lambda}{2n}\right)^2 \Delta v_B^2$$

wherein $\Delta v_B$ is the at least one Brillouin frequency shift, $\rho$ is a density of the at least a portion of the reproductive cellular structure, $\lambda$ is a vacuum wavelength of the radiation, and n is a refractive index of the at least a portion of the reproductive cellular structure.

4. The method of claim 3, further comprising:
measuring a width of at least one Brillouin peak in the frequency spectrum of the detected scattered radiation;
deriving the modulus of viscosity M" using the following formula:

$$M'' = \rho\left(\frac{\lambda}{2n}\right)^2 \Delta v_B \Gamma_B$$

wherein $\Gamma_B$ is the width of the at least one Brillouin peak; and
deriving a complex modulus M* using the following formula:

$$M^* = M' + i\, M''$$

wherein said i denotes a unit imaginary number which satisfies $i^2 = -1$.

5. The method of claim 2, wherein at least one of the modulus of elasticity or the modulus of viscosity is determined with a sub-cellular resolution.

6. The method of claim 5, further comprising:
determining at least one of the modulus of elasticity or the modulus of viscosity at a plurality of sub-cellular locations of the reproductive cellular structure.

7. The method of claim 1, wherein the illuminating radiation is laser radiation.

8. The method of claim 7, wherein the laser radiation includes at least one frequency component corresponding to a vacuum wavelength in a range of about 400 nm to about 800 nm.

9. The method of claim 1, further comprising:
filtering out radiation that is elastically scattered from the reproductive cellular structure to facilitate detection of the at least one Brillouin frequency shift.

10. The method of claim 1,
wherein the frequency spectrum of the scattered radiation is obtained using a spectrometer.

11. A method comprising:
obtaining a modulus of elasticity of at least a portion of a reproductive cellular structure using Brillouin spectroscopy; and
determining a viability index of the reproductive cellular structure based on the modulus of elasticity.

12. The method of claim 11, further comprising obtaining a modulus of viscosity of at least a portion of the reproductive cellular structure using the Brillouin spectroscopy.

13. The method of claim 11, wherein the reproductive cellular structure includes one selected from the group consisting of an embryo, a morula, a blastula, gastrula, a zygote, an ovum, and an oocyte.

14. The method of claim 11, wherein the reproductive cellular structure comprises an oocyte, and
wherein the method is performed to select the oocyte to be fertilized with a male gamete.

15. The method of claim 11, wherein the reproductive cellular structure comprises a zygote, and
wherein the method is performed to select the zygote to proceed further into in vitro fertilization.

16. The method of claim 11, wherein the reproductive cellular structure comprises an embryo, and wherein the method is performed to select the embryo to be transferred to a uterus.

* * * * *